United States Patent [19]

Fiedler et al.

[11] Patent Number: 4,487,966
[45] Date of Patent: Dec. 11, 1984

[54] 3-AMINOMETHYL-1-(3-AMINOPROPYL-1-METHYL)-4-METHYLCYCLOHEXANE, A PROCESS FOR ITS PREPARATION AND ITS USE

[75] Inventors: Paul Fiedler, Cologne; Rudolf Braden, Odenthal, both of Fed. Rep. of Germany

[73] Assignee: Bayer Aktiengesellschaft, Leverkusen, Fed. Rep. of Germany

[21] Appl. No.: 514,376

[22] Filed: Jul. 15, 1983

[30] Foreign Application Priority Data

Jul. 31, 1982 [DE] Fed. Rep. of Germany ....... 3228719

[51] Int. Cl.$^3$ .................. C07C 87/34; C07C 87/36
[52] U.S. Cl. ................... 564/454; 564/445; 564/446
[58] Field of Search .................. 564/454, 445, 446

[56] References Cited

U.S. PATENT DOCUMENTS

| | | | |
|---|---|---|---|
| 3,565,954 | 2/1971 | Bouniot | 564/446 X |
| 3,597,438 | 8/1971 | Brake | 564/446 X |
| 4,009,209 | 2/1977 | Leupold et al. | 564/454 X |
| 4,020,059 | 4/1977 | Maeda et al. | 564/446 X |
| 4,101,578 | 7/1978 | Bock et al. | 564/454 |
| 4,207,260 | 6/1980 | Imai | 564/446 X |
| 4,317,932 | 3/1982 | Jachimowicz | 564/446 X |

*Primary Examiner*—Paul F. Shaver
*Attorney, Agent, or Firm*—Sprung, Horn, Kramer & Woods

[57] ABSTRACT

3-Aminomethyl-1-(3-aminopropyl-1-methyl)-4-methylcyclohexane and a process for the preparation of this new compound, which uses limonene and/or monohydroformylation products of limonene as starting substances and proceeds via a dihydroformylation product of limonene. The new compound is useful as a corrosion inhibitor, as a crosslinking agent for epoxide resins and as a chain lengthening agent for NCO prepolymers.

1 Claim, No Drawings

3-AMINOMETHYL-1-(3-AMINOPROPYL-1-METHYL)-4-METHYLCYCLOHEXANE, A PROCESS FOR ITS PREPARATION AND ITS USE

The present invention relates to the new chemical compound 3-aminomethyl-1-(3-aminopropyl-1-methyl)-4-methylcyclohexane, a process for its preparation, in which a dihydroformylation product of limonene is first formed starting from limonene and/or monohydroformylation products of limonene and the compound according to the invention is obtained therefrom, and to the use of the new compound as a corrosion inhibitor, as a crosslinking agent for epoxy resins and as a chain lengthening agent for NCO prepolymers.

The new chemical compound 3-aminomethyl-1-(3-aminopropyl-1-methyl)-4-methyl-cyclohexane can be characterised by the formula

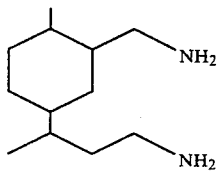

and in the following text is also called the diamine according to the invention.

Eight different diastereomeric forms of the diamine according to the invention exist, and these are usually in the form of a mixture of all or some of the diastereomers. The individual diastereomers can be enriched or isolated from such mixtures by conventional methods of diastereomer separation, for example by capillary gas chromatography (capillary GC) or high pressure liquid chromatography (HPLC).

The process according to the invention for the preparation of 3-aminomethyl-1-(3-aminopropyl-1-methyl)-4-methyl-cyclohexane is characterised in that limonene and/or monohydroformylation products of limonene are reacted with carbon monoxide and hydrogen at temperatures from 80° to 180° C. under pressures from 20 to 1,000 bar in the presence of a rhodium-containing catalyst which, in addition to rhodium, contains at least one ligand from the group comprising carbon monoxide, alkenes with 2 to 12 C atoms and organic compounds containing nitrogen, sulphur, oxygen or phosphorus, in an amount which corresponds to less than 1 g of rhodium per kg of starting material, and the resulting dihydroformylation product of limonene is then treated with hydrogen at 50° to 150° C. in the presence of ammonia and a hydrogenation catalyst.

Limonene (4-isopropenylmethylcyclohexene) of any desired origin can be used in the process according to the invention. Limonene in the form of enantiomer mixtures, for example d,l-limonene, as an enantiomer mixture in which one enantiomer is enriched, or in the form of a pure enantiomer, for example as (R),(+)-limonene or (S),(−)-limonene, can be used. Limonene is accessible, for example, by extraction from natural materials, in particular from citrus fruits and certain types of conifers.

Monohydroformylation products of limonene can also be used in the process according to the invention, for example 4-methyl-cyclohex-3-ene-β-methylpropanal. The monohydroformylation of limonene is known, see, for example, K. Kogami, Japan Yakagaku 22 (6), page 316 (1973). The monohydroformylation products of limonene can be used in the form of the reaction mixture obtained in the monohydroformylation of limonene, preferably after the catalyst used has been separated off. Monohydroformylation products of limonene which are obtained after distillative working up of the reaction mixture from the monohydroformylation of limonene are also suitable.

Any desired mixtures of limonene and monohydroformylation products of limonene can furthermore be used in the process according to the invention.

The reaction according to the invention of limonene and/or monohydroformylation products of limonene with carbon monoxide and hydrogen is carried out in the presence of a rhodium-containing catalyst which, in addition to rhodium, contains at least one ligand from the group comprising carbon monoxide, alkenes with 2 to 12 C atoms and organic compounds containing nitrogen, sulphur, oxygen or phosphorus. Rhodium-containing catalysts which are soluble in the reaction mixture are preferred. The rhodium-containing catalysts can also contain several similar or different ligands of the abovementioned type, and in addition anionic radicals, for example halogen atoms and/or acetate radicals.

Suitable ligands from the group comprising alkenes with 2 to 12 C atoms can be open-chain, cyclic or bicyclic and contain one or more olefinic double bonds. Such ligands preferably contain two olefinic double bonds. Examples which may be mentioned are bicyclo[2.2.1]hepta-1,4-diene and cycloocta-1,5-diene.

Examples of suitable ligands from the group comprising organic compounds containing nitrogen are amines. Tertiary amines are preferred, especially aromatic and heterocyclic tertiary amines. Examples which may be mentioned are pyridine, picolines, ethylpyridines, N-methylpyrrolidine, N-methylpyrrole, N,N'-dimethylpiperazine, dimethylcyclohexylamine, triethylamine, N,N-dimethylaniline, N-methylmorpholine, N-methylindole, quinoline, isoquinoline and N-methylpyrrolidone.

Examples of suitable ligands from the group comprising organic compounds containing sulphur are organic disulphides and sulphoxides. Examples which may be mentioned are dibenzyl sulphide, di-n-butyl sulphide, dimethyl sulphoxide, diethyl sulphoxide, di-(4-chlorobenzyl) sulphide, di-(4-cyanobenzyl) sulphide, bis-(4-dimethylaminobenzyl) sulphide, di-(4-diethylaminobenzyl) sulphide, di-(α-naphthylmethyl) sulphide, di-(2,6-dichlorobenzyl) sulphide, di-(3,4-dichlorobenzyl) sulphide, di-(2-chlorobenzyl) sulphide, di-(5,6,7,8-tetrahydronaphth-2-yl-methyl) sulphide, benzyl methyl sulphide, benzyl dodecyl sulphide, 4-dimethylaminobenzyl methyl sulphide, benzyl butyl sulphide, bis-(4-carboxybenzyl) sulphide, di-(4-methylbenzyl) sulphide, di-(3-methylbenzyl) sulphide and di-(2-methylbenzyl) sulphide.

Examples of suitable ligands from the group comprising organic compounds containing oxygen are unsubstituted and substituted acetylacetonates. Examples of substituted acetylacetonates are those which contain alkyl, phenyl, substituted phenyl and/or fluoroalkyl groups. Examples which may be mentioned of ligands from the group comprising organic compounds containing oxygen are 1,1,1-trifluoropenta-2,4-dione, benzoylacetone and 2-acetylcyclopentanone.

Examples of suitable ligands from the group comprising organic compounds containing phosphorus are triorganophosphorus ligands. Tertiary organic phosphines and phosphites which contain identical or different alkyl radicals with 1 to 20 C atoms, cycloalkyl radicals with 5 to 12 C atoms and aralkyl radicals with 7 to 10 C atoms and at least one aryl radical with 3 to 10 C atoms are particularly suitable. These alkyl, cycloalkyl, aralkyl and aryl radicals may carry substituents, for example 1 to 3 hydroxyl groups, alkoxy and/or carbalkoxy groups with 1 to 4 C atoms, optionally substituted amino groups and/or halogen atoms. Examples which may be mentioned of ligands from the group comprising organic compounds containing phosphorus are triphenyl phosphine, diethylphenyl phosphine, tritolyl phosphine, trinaphthyl phosphine, diphenylmethyl phosphine, diphenylbutyl phosphine, tris-(p-chlorophenyl) phosphine, tris-(p-carbomethoxyphenyl) phosphine, tris-(p-cyanophenyl) phosphine, diphenylphosphonous acid phenyl ester, benzenephosphonous acid diphenyl ester, triphenyl phosphite, $P[CH_2CH_2CH_2N(CH_3)_2]_3$, $P[CH_2CH_2CH_2N(C_2H_5)_2]_3$, $P(CH_2CH_2CH_2-NH-iso-C_4H_9)_3$, $P[CH_2CH_2CH_2N(iso-C_4H_9)_2]_3$, $(n-C_4H_9)_2PCH_2CH_2N(C_2H_5)_2$, $P[CH_2N(C_2H_5)_2]_3$ $P[C_6H_4N(CH_3)_2]_3$, $P[CH_2CH_2C_6H_4N(C_2H_5)_2]_3$,

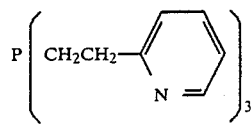

$P[CH_2CH_2CH_2N(tert.C_4H_9)_2]_3$ and $P[CH_2CH_2CH_2N(iso-C_3H_7)_2]_3$.

Of the tertiary organic phosphines and phosphites, the triaryl phosphines and triaryl phosphites are preferred.

Other suitable ligands from the group comprising organic compounds containing phosphorus are complex ligands which consist of triorganophosphines partly substituted by ferrocene, such as are described, for example, in German Offenlegungsschrift No. 2,617,306.

Preferred rhodium-containing catalysts for the process according to the invention are those which correspond to one of the formulae $XRh(CO)L_2$, $XRh(CO)L_3$, $RhxL_3$, $[Rh(CO)_2L_2]_2$ and $[Rh(OCOCH_3)(CO)L]_2$ in which X denotes a chlorine, bromine or iodine atom and L denotes one of the ligands described above.

Particularly preferred rhodium-containing catalysts for the process according to the invention are dimeric rhodiumcarbonyl-chloride, $Rh_2(C_8H_{12})_2Cl_2$, $Rh(CO)_2acac$, $Rh[(C_5H_5)_2Fe]Pph_2]_3Cl_3$, $Rh[(C_6H_5CH_2)_2S]_3Cl_3$, $Rh(Pph_3)_3Cl$, $Rh(Pph_3)_3Br$, $Rh(Pph_3)_3Cl_3$, rhodium 2-ethylhexanoate, $Rh[(4-CH_3O-C_6H_4CH_2)_2S]_3Cl_3$, $Rh[(4-Cl-C_6H_4CH_2)_2S]_3Cl_3$, $Rh[(C_6H_5CH_2)_2SO]_3Cl_3$ and $Rh[CH_3)_2SO]_3Cl_3$ in which acac represents an acetylacetonate radical and Ph represents a phenyl group.

The rhodium-containing catalysts described above do not have to be employed as such in the process according to the invention. It may be advantageous to add a rhodium salt and one or more ligands separately to the process according to the invention and thus to dispense with separate preparation of rhodium complex compounds. Moreover, it is generally possible to replace some of the rhodium by cobalt. In general, up to 95% by weight of the rhodium, preferably up to 90% by weight of the rhodium, can be replaced by cobalt.

According to the invention, the rhodium-containing catalysts are employed in an amount which corresponds to less than 1 g of rhodium (calculated as the metal) per kg of limonene and/or monohydroformylation products of limonene (=starting material) employed. Preferably, 1 to 1,000 mg, and particularly preferably 10 to 600 mg, of rhodium (calculated as the metal) are employed per kg of starting material.

The hydroformylation according to the invention is carried out, inter alia, in the liquid phase. The rhodium-containing catalyst may also be attached to a solid carrier, such as is described, for example, by P. I. Division et al. in Catalysis, Volume 1 (1976), pages 391–395.

In the simplest case, the liquid phase is a mixture of the substances present (starting material(s), reaction product(s) and rhodium-containing catalyst). However, the reaction can also be carried out in the presence of one or more solvents which are inert or substantially inert under the reaction conditions and which is able to dissolve the rhodium-containing catalyst. Examples of suitable solvents are alkyl-substituted benzenes, higher-boiling esters, such as dialkyldicarboxylates and esters of polyols, such as esters of trimethylolpropane or pentaerythritol, higher-boiling ketones, higher-boiling alcohols, such as butanols, higher-boiling ethers and higher-boiling hydrocarbons, such as saturated aliphatic and cycloaliphatic hydrocarbons.

If solvents are used, those which are also suitable for the subsequent treatment with hydrogen in the presence of ammonia are preferred. Examples of these solvents which may be mentioned are benzene, toluene, xylene, isopropanol, methylcyclohexane, decalin, dioxane, tetrahydrofuran, ethylene glycol monoethyl ether and diethylene glycol dimethyl ether.

In the reaction according to the invention of limonene and/or monohydroformylation products of limonene with carbon monoxide and hydrogen, carbon monoxide and hydrogen are generally used in at least the amounts theoretically required for complete formation of a dihydroformylation product of the limonene. The carbon monoxide and hydrogen are preferably used in excess, for example in an excess of in each case up to 1,000 mol %. The carbon monoxide and hydrogen can be used in various proportions relative to one another. For example, the volume ratio of carbon monoxide to hydrogen can be from 4:1 to 1:4. This ratio is preferably 2:1 to 1:1. About the same amounts by volume of carbon monoxide and hydrogen are preferably used.

The reaction according to the invention of limonene and/or monohydroformylation products of limonene with carbon monoxide and hydrogen is carried out at temperatures from 80° to 180° C. under pressures from 20 to 1,000 bar. Preferably, the temperature is in the range from 105° to 180° C. and the pressure is in the range from 100 to 400 bar. Temperatures in the range from 120° to 170° C. are particularly preferred.

It may be advantageous to carry out the hydroformylation stepwise, first at a lower temperature, for example at 80° to 140° C., and then at a higher temperature, for example 130° to 180° C. It may also be advantageous to add some of the catalyst, the solvent and/or the starting material only during the reaction.

The reaction mixture obtained after the reaction according to the invention of limonene and/or monohydroformylation products of limonene with carbon monoxide and hydrogen can be used directly in the treatment with hydrogen in the presence of ammonia (reductive amination). In particular, it is not necessary to separate off the rhodium-containing catalyst, which can be advantageous from an economic point of view, since the removal of the very small amounts of catalyst can be expensive. However, it is also possible to separate off the catalyst from the reaction mixture, for example by distillation or extraction, and, where relevant, to re-use it. Moreover, it may be advantageous to separate off the dihydroformylation product of limonene from the reaction product, for example by distillation, and to use only this product in the subsequent reductive amination. Any monohydroformylation products still present can likewise be separated off thereby, and where relevant fed to a renewed reaction with carbon monoxide and hydrogen.

The reductive amination according to the invention is in general carried out in the presence of at least 2 mols of ammonia per mol of dihydroformylation product of limonene. An excess of ammonia is preferably used, for example 3 to 20 mols of ammonia per mol of dihydroformylation product of limonene.

The reductive amination according to the invention is carried out in the presence of a hydrogenation catalyst. Examples of suitable catalysts are those which contain, as the active component, one or more elements of atomic number 23 to 29 in metallic and/or oxidic form.

Examples of suitable catalysts are nickel or cobalt catalysts, such as nickel-on-supports, supports which may be used being inorganic materials, such as kieselguhr, silicic acids, aluminum oxides, silicates, aluminum silicates, montmorillonite, zeolites, spinel, dolomite, kaolin, magnesium silicates, zirconium oxide, iron oxide, zinc oxide, calcium carbonate, silicon carbide, aluminum phosphate, boron phosphate, asbestos or active charcoal, and organic supports for catalysts which can be used being naturally occurring or synthetic compounds of high molecular weight, such as silk, polyamides, polystyrenes, cellulose or polyurethanes. The supports can be, for example, in the form of beads, strands, filaments, cylinders or polygons or in powder form. Other suitable catalysts are Raney type catalysts, such as Raney nickel, W-1-, W-5-, W-6- and W-7-Raney nickel, as described by H. Adkins, J.Am.Chem.Soc. 69, 3039 (1974), Raney cobalt catalysts, Raney copper, Raney nickel/iron, Raney cobalt/nickel and Raney cobalt/iron, metal catalysts prepared by reduction of nickel salts or cobalt salts, such as Urushibara nickel, nickel salts or cobalt salts reduced with metal-alkyl compounds, alkali metal hydrides, hydrazine, boranates or boron hydride, catalysts prepared by reduction of metal oxides or metal oxide mixtures, and metal oxides or oxide mixtures.

The reduction of the metal oxides or metal salts can also be carried out with hydrogen, if appropriate at elevated temperature and under increased pressure, under the conditions of the process or during the process.

The catalysts can contain up to 10% by weight of one or more of the following elements as accelerators: Li, Na, Ca, Ba, K, Ag, Be, La, Ce, Ti, V, Nb, Ta, Mo and W, and up to 1% of the elements Ru, Rh, Pd, Au, Ir and Pt.

Particularly preferred hydrogenation catalysts are Raney catalysts, such as Raney nickel, Raney cobalt and Raney nickel/iron.

0.01 to 10% by weight of hydrogenation catalyst is generally used. Preferably, 0.1 to 5% by weight of hydrogenation catalyst is used.

The reductive amination according to the invention is carried out at 50° to 150° C. Temperatures of 90° to 135° C. are preferred. The hydrogen pressure during the amination should generally be greater than 10 bar. Hydrogen pressures of 50 to 200 bar are preferred.

The reductive amination according to the invention can be carried out in the presence or absence of solvents. Suitable solvents are described above. The reaction mixture can also be diluted with the diamine according to the invention. The reaction is preferably carried out with a weight ratio of dihydroformylation product to solvent of 1:3 to 3:1.

It is possible to carry out the reductive amination according to the invention continuously or batchwise.

It may be advantageous first to prepare the Schiff's base from the dihydroformylation product of limonene and ammonia, if desired in the presence of a solvent, to separate off the water thereby liberated, for example by phase separation, and only then to carry out the treatment with hydrogen. It may moreover be advantageous to initially introduce the hydrogenation catalyst, ammonia and a solvent or diamine according to the invention which has already been prepared into a hydrogenation autoclave under a hydrogen pressure and to pump in the dihydroformylation product of limonene, if desired together with a solvent. Finally, it may also be advantageous to carry out the reductive amination according to the invention with addition of a catalytic amount of an acid. Such acids can be inorganic acids, such as phosphoric acid, or organic acids, such as acetic acid, propionic acid or succinic acid. The addition of acids in amounts of 0.1 to 3% by weight (based on the dihydroformylation product employed) is preferred.

The reductive amination according to the invention usually proceeds very selectively. For example, 90 to 99% of the limonenedialdehyde employed is converted into the diamine according to the invention. If pure or substantially pure limonenedialdehyde has been used in the reductive amination, sufficiently pure diamine according to the invention can therefore be obtained if, after the reductive amination, only the hydrogenation catalyst is separated off, for example by filtration or centrifugation, and also, if necessary, the solvent. In other cases, especially if a crude dihydroformylation product of limonene has been used in the reductive amination, it is generally necessary to work up the reaction mixture further, after the hydrogenation catalyst has been separated off, for example by distillation or rectification, in order to obtain sufficiently pure diamine according to the invention.

As described above, the diamine according to the invention is generally obtained as a mixture of some or all the enantiomeric forms. The composition of this mixture depends, inter alia, on the starting material, in particular on whether R(+)-limonene, S(+)-limonen, d,l-limonene or a certain mixture of these enantiomeric limonenes has been employed.

The present invention furthermore relates to the use of 3-aminomethyl-1-(3-aminopropyl-1-methyl)-4-methylcyclohexane as a corrosion inhibitor, a crosslinking agent for epoxide resins and a chain lengthening agent for NCO prepolymers, which are used, for example, for the preparation of polyurethane-polyureas. The diamine according to the invention is excellently compatible with heating oils, lubricants and propelling agents based on hydrocarbons, and can therefore advantageously be added to such substances as a corrosion inhibitor, for example in amounts of 0.01 to 1% by weight. If the diamine according to the invention is used as a crosslinking agent for epoxide resins or as a chain lengthening agent for NCO prepolymers, it is added, for example, in those amounts in which other diamines are used for this purpose. The type of diastereomer mixture of the diamine according to the invention is of no importance for the given uses.

The present invention provides for the first time an industrially interesting diamine which is accessible from the new generation raw material limonene.

It is extremely surprising that it is possible, according to the invention, to obtain good yields of 3-aminomethyl-1-(3-aminopropyl-1-methyl)-4-methyl-cyclohexane from limonene. In particular, no industrially useful process has hitherto been disclosed for the preparation of dihydroformylation products of limonene.

Thus, K. Kogami, Japan Yakagaku 22 (6), page 316 (1973) describes a process for the hydroformylation of limonene in which 4-methylcyclohex-3-ene-$\beta$-methylpropanal (which is a monohydroformylation product of limonene) is obtained in 45 to 52% yield and the dihydroformylation product of limonene is obtained in a maximum of 16% yield, using cobalt carbonyl as the catalyst. If rhodium trichloride$\times 3H_2O$ is used as the catalyst in the same process in an amount of 1.7 to 3.4 g of rhodium per kg of limonene, the dihydroformylation product of limonene is obtained in a yield of only 2 to 7%.

Hydroformylations of limonene in various solvents are described in Ind.Eng.Chem.Proc.Res.Dev. 4, 283 (1965). Complex mixtures of the monohydroformylation products which contain only a little dihydroformylation product are always obtained.

Although European Offenlegungsschrift No. 54,986 discloses an improvement in the preparation of 4-methylcyclohex-3-ene-$\beta$-methylpropanal, there are no instructions of how the second double bond present in limonene, that is to say the methyl-substituted double bond in the ring, can be hydroformylated.

E. Falbe, New Syntheses with Carbon Monoxide, Springer-Verlag Heidelberg, page 117 (1980) also gives no indication as to how dihydroformylation products of limonene can be obtained.

This prior art provided a substantial bias to the expert against attempting to prepare the diamine according to the invention from limonene via the intermediate stage of the dihydroformylation products of limonene. It could in no way be expected that dihydroformylation products of limonene are accessible in selectivities of over 75% with smaller amounts of a modified rhodium catalyst than those in the literature reference of K. Kogami, and the diamine according to the invention is accessible therefrom in yields of over 90%.

EXAMPLES

Example 1

(a) Hydroformylation 100 g of limonenemonoaldehyde (4-methylcyclohex-3-ene-$\beta$-methylpropanal), 300 ml of cyclohexane and 0.1 g of dimeric rhodium carbonyl-chloride were introduced into a stainless steel autoclave of 700 ml capacity and were heated to 145° C. under water gas (CO/H$_2$), while stirring. The pressure was kept between 200 and 220 bar by regularly forcing in more water gas. After 2 hours, the pressure remained constant. The autoclave was cooled and let down and the reaction mixture was separated into its components by thin film distillation. 75 g of limonenedialdehyde (4-methyl-3-formylcyclohexane-$\beta$-methylpropanal) were obtained at 150° C. under 0.05 mbar, corresponding to a selectivity of 75%.

IR (cm$^{-1}$): 2,920, 2,720, 1,725, 1,450, 1,380.

(b) Reductive amination 135 g of limonenedioaldehyde (4-methyl-3-formylcyclohexane-$\beta$-methylpropanal), 300 ml of tetrahydrofuran and 10 g of Raney nickel were initially introduced into a stainless steel autoclave of 1.3 liters capacity and were stirred. After 300 ml of liquid ammonia had been forced in, the mixture was heated to 100° C. and was kept at this temperature for 1 hour. Hydrogenation was then carried out with hydrogen at 120° C. under an overall pressure of 140 bar. The pressure was kept at 140 bar by regularly forcing in more hydrogen. After 3 hours, the pressure remained constant. The autoclave was cooled and let down, the catalyst was separated off and the reaction mixture was separated into its components by distillation. 117 g of 3-aminomethyl-1-(3-aminopropyl-1-methyl)-4-methylcyclohexane were obtained at 147° to 156° C. under a pressure of 0.05 mbar, which corresponds to a selectivity of 87%. The equivalent weight of the diamine was determined by titration with 1N HCl, and was found to be 100.2 g per mol (calculated: 99 g per mol).

IR (cm$^{-1}$): 3,300, 2,900, 1,600, 1,450, 1,380, 830.

Example 2

300 g of limonene, 500 ml of cyclohexane and 0.3 g of Rh$_2$(C$_8$H$_{12}$)$_2$Cl$_2$ were heated to 150° C. in a 1.3 liter stainless steel autoclave under water gas pressure, while stirring. The pressure was kept between 200 and 220 bar by regularly forcing in more water gas. When the reaction had ended, the autoclave was cooled and let down and the reaction mixture was separated into its components by distillation. The small amounts of monoaldehyde obtained (boiling point 90° C./0.1 mbar) were hydroformylated further as described in Example 1a. The resulting dialdehyde (boiling point 150° C./0.05 mbar) was further processed as described in Example 1b.

Example 3

250 g of limonenemonoaldehyde, 750 ml of toluene and 0.26 g of Rh[[(C$_5$H$_5$)$_2$Fe]Pph$_2$]$_3$Cl$_3$ were heated to 145° C. in a stainless steel autoclave of 1.6 liter capacity under water gas pressure (CO/H$_2$ 1:1), while stirring. The pressure was kept between 200 and 280 bar by regularly forcing in more water gas. After about 2 hours, the pressure remained constant and the autoclave was cooled and let down. Analysis of the product by gas chromatography showed a dialdehyde content of 21%, which corresponds to a yield of 70% and a selectivity of 81%.

What is claimed is:

1. 3-Aminomethyl-1-(3-aminopropyl-1-methyl)-4-methylcyclohexane.

* * * * *